United States Patent
Schindler et al.

(10) Patent No.: US 6,627,628 B1
(45) Date of Patent: Sep. 30, 2003

(54) SUBSTITUTED 4-AMINO-2-ARYL-CYCLOPENTA[D]PYRIMIDINES, THEIR PRODUCTION AND USE AND PHARMACEUTICAL PREPARATIONS CONTAINING SAME

(75) Inventors: Ursula Schindler, Soden (DE); Karl Schoenafinger, Alzenau (DE); Hartmut Strobel, Liederbach (DE)

(73) Assignee: Aventis Pharma Deutschland, GmbH, Frankfurt am Main (DE)

(*) Notice: Subject to any disclaimer, the term of this patent is extended or adjusted under 35 U.S.C. 154(b) by 0 days.

(21) Appl. No.: 09/856,069

(22) PCT Filed: Nov. 3, 1999

(86) PCT No.: PCT/EP99/08382

§ 371 (c)(1), (2), (4) Date: May 17, 2001

(87) PCT Pub. No.: WO00/31047

PCT Pub. Date: Jun. 2, 2000

(30) Foreign Application Priority Data

Nov. 19, 1998 (DE) .......................... 198 53 278

(51) Int. Cl.⁷ .................... C07D 239/70; C07D 401/12; A61K 31/517
(52) U.S. Cl. .................. 514/228.2; 514/234.5; 514/258.1; 544/61; 544/116; 544/253
(58) Field of Search .......... 544/61, 116, 253; 514/228.2, 234.5, 258.1

(56) References Cited

U.S. PATENT DOCUMENTS

| | | | |
|---|---|---|---|
| 3,322,759 A | 5/1967 | Carney et al. | 260/247.5 |
| 3,346,452 A | 10/1967 | Carney et al. | 167/65 |

FOREIGN PATENT DOCUMENTS

| | | |
|---|---|---|
| DE | 40 29 654 A1 | 4/1992 |
| EP | 667 345 A1 | 8/1995 |
| EP | 826 673 A1 | 3/1998 |
| JP | 07228573 | 8/1995 |
| WO | WO 92/05159 | 4/1992 |
| WO | WO 97/47601 | 12/1997 |
| WO | WO 98/16223 | 4/1998 |
| WO | WO 98/16507 | 4/1998 |
| WO | WO 00/09496 | 2/2000 |

OTHER PUBLICATIONS

Adnot et al., PubMed Abstract (Arch. Mal. Coeur. Vaiss. 87 Spec. No. 4:41–51), Dec. 1994.*
Ayajiki et al., PubMed Abstract (Nippon Yakurigaku Zasshi, 119(1):21–8), Jan. 2002.*
Louis J. Ignarro, Regulation of Cytosolic Guanylyl Cyclase by Porphyrins and Mettalloporphyrins, Advances in Pharmacology, vol. 26, 1994, pps 35–65.
Feng–Nien Ko et al., YC–1, a Novel Activator of Platelet Guanylate Cyclase, Blood, vol. 84, No. 12, Dec. 1994, pps 4225–4233.
Alexander Mülsch et al., Purification of Heme–Containing Soluble Guanylyl Cyclase, Methods in Enzymology, vol. 195, 1991, pps 378–383.
Douglas J. Pettibone et al., A Structurally Novel Stimulator of Guanylate Cyclase With Long–Lasting Hypotensive Activity In The Dog, European Journal of Pharmacology, 116, 1985, pps 307–312.
D.L. Vesley, B Complex Vitamins Activate Rat Guanylate Cyclase and Increase Cyclid GMP Levels, European Journal of Clinical Investigation 15, 1985, pps 258–262.
Daivd L. Vesley, Phencyclidine Stimulates Guanylate Cyclase Activity, Biochemical and Biophysical Research Communications, vol. 88, No. 4, Jun. 27, 1979, pps 1244–1248
Chin–Chung Wu et al., YC–1 Inhibited Human Platelet Aggregation Through NO–Independent Activation of Soluble Guanylate Cyclase, British Journal of Pharmacology, 116, 1995, pps 1973–1978.
Sheu M. Yu et al., Mechanism of Anti–proliferation caused by YC–1, an indazole derivative, In Cultured Rat A10 Vascular Smooth–Muscle Cells, Biochem. J. 306, 1995, pps 787–792.
Sheu–Meei Yu et al., Vasorelaxant Effect of Isoliquiritigenin, a Novel Soluble Guanylate Cyclase Activator, in Rat Aorta, British Journal of Pharmacology, 114, 1995, pps 1587–1594.
EPO Patent Abstract of Japan, Japanese Publication No. 07228573, Aug. 1995.

\* cited by examiner

Primary Examiner—Deepak Rao
(74) Attorney, Agent, or Firm—Finnegan, Henderson, Farabow, Garrett & Dunner, LLP

(57) ABSTRACT

The present invention relates to compounds of formula (I) wherein $R^1$, $R^2$ and $R^3$ have the meanings given in the claims. Said compounds are valuable active agents in medicaments for the treatment and prophylaxis of diseases, for example cardiovascular diseases such as hypertension, angina pectoris, heart failure, thrombosis and atherosclerosis. The compounds of formula (I) are able to modulate the body's own production of cyclic guanosine monophosphate (cGMP) and are generally suitable for the treatment and prophylaxis ofisorders associated with an impaired cGMP balance. The invention also relates to methods for producing compounds of formula (I), to their use in the treatment and prophylaxis of the above diseases and in the preparation of medicaments for such diseases, and to pharmaceutical preparations containing the compounds of formula (I).

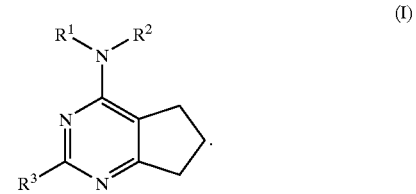

11 Claims, No Drawings

SUBSTITUTED 4-AMINO-2-ARYL-CYCLOPENTA[D]PYRIMIDINES, THEIR PRODUCTION AND USE AND PHARMACEUTICAL PREPARATIONS CONTAINING SAME

This application is a nation stage filing of International Application No. PCT/EP99/08382, filed Nov. 3, 1999. This application also claims the benefit of priority under 35 U.S.C. §119(a) to German Patent Application No. 198 53 278.4, filed on Nov. 19, 1998.

The present invention relates to compounds of the formula I,

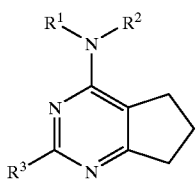

in which $R^1$, $R^2$ and $R^3$ have the meanings indicated below, which are valuable pharmaceutical active compounds for the therapy and prophylaxis of diseases, for example of cardiovascular disorders such as high blood pressure, angina pectoris, cardiac insufficiency, thromboses or atherosclerosis. The compounds of the formula I have the ability to modulate the endogenous production of cyclic guanosine monophosphate (cGMP) and are generally, suitable for the therapy and prophylaxis of disease states which are associated with a disturbed cGMP balance. The invention furthermore relates to processes for the preparation of compounds of the formula I, their use for the therapy and prophylaxis of the designated disease states and for the production of pharmaceuticals therefor, and pharmaceutical preparations which contain compounds of the formula I.

cGMP is an important intracellular messenger, which elicits a number of pharmacological effects by means of the modulation of cGMP-dependent protein kinases, phosphodiesterases and ion channels. Examples are smooth muscle relaxation, the inhibition of platelet activation and the inhibition of smooth muscle cell proliferation and leukocyte adhesion. cGMP is produced by particulate and soluble guanylate cyclases as a response to a number of extracellular and intracellular stimuli. In the case of the particulate guanylate cyclases, the stimulation essentially takes place by means of peptide signal substances, such as the atrial natriuretic peptide or the cerebral natriuretic peptide. The soluble guanylate cyclases (sGC), which are cytosolic, heterodimeric heme proteins, however, are essentially regulated by a family of low molecular weight, enzymatically formed factors. The most important stimulant is nitrogen monoxide (NO) or a closely related species. The importance of other factors such as carbon monoxide or the hydroxyl radical is still largely unclarified. The binding of NO to the heme with formation of a pentacoordinated heme-nitrosyl complex is discussed as an activation mechanism of activation by NO. The release associated therewith of the histidine which is bound to the iron in the basal state converts the enzyme into the activated conformation.

Active soluble guanylate cyclases are each composed of one α- and one β-subunit. Several subtypes of the subunits are described, which differ from one another with respect to sequence, tissue-specific distribution and expression in various stages of development. The subtypes $\alpha_1$ and $\beta_1$ are mainly expressed in the brain and lung, while $\beta_2$ is especially found in liver and kidney. The subtype $\alpha_2$ was detected in human fetal brain. The subunits designated as ($\alpha_3$ and $\beta_3$ were isolated from human brain and are homologous to $\alpha_1$ and $\beta_1$. More recent studies point to an $\alpha_{2i}$ subunit, which contains an insert in the catalytic domain. All subunits show great homology in the area of the catalytic domain. The enzymes probably contain one heme per heterodimer, which is bonded via $\beta_1$-Cys-78 and/or $\beta_1$-His-105 and is part of the regulatory center.

The formation of guanylate cyclase-activating factors can be decreased under pathological conditions, or increased degradation thereof can take place as a result of the increased occurrence of free radicals. The decreased activation of the sGC resulting therefrom leads, via the attenuation of the respective cGMP-mediated cell response, for example, to an increase in the blood pressure, to platelet activation or to increased cell proliferation and cell adhesion. As a result, the formation of endothelial dysfunction, atherosclerosis, high blood pressure, stable and unstable angina pectoris, thromboses, myocardial infarct, strokes or erectile dysfunction occurs. The pharmacological stimulation of the sGC offers a possibility for the normalization of cGMP production and thus allows the treatment or prevention of diseases of this type.

For the pharmacological stimulation of sGC, until now compounds were almost exclusively used whose action is based on an intermediate release of NO, for example organic nitrates. The disadvantage of this method of treatment lies in the development of tolerance and weakening of action and the higher dose which therefore becomes necessary.

Various sGC stimulators which do not act via a release of NO were described in a series of publications by Vesely. The compounds, which are mostly hormones, plant hormones, vitamins or, for example, natural substances such as lizard toxins, however, consistently show only weak effects on cGMP formation in cell lysates (D. L. Vesely, Eur. J. Clin. Invest. 15 (1985) 258; D. L. Vesely, Biochem. Biophys. Res. Comm. 88 (1979) 1244). Stimulation of heme-free guanylate cyclase by protoporphyrin IX was detected by Ignarro et al. (Adv. Pharmacol. 26 (1994) 35). Pettibone et al. (Eur. J. Pharmacol. 116 (1985) 307) described a hypotensive action for diphenyliodonium hexafluorophoshate and attributed this to a stimulation of sGC. Isoliquiritiginin, which shows a relaxant action on isolated rat aortas, likewise activates sGC according to Yu et al. (Brit. J. Pharmacol. 114 (1995) 1587). Ko et al. (Blood 84 (1994) 4226), Yu et al. (Biochem. J. 306 (1995) 787) and Wu et al. (Brit. J. Pharmacol. 116 (1995) 1973) detected an sGC stimulating activity of 1-benzyl-3-(5-hydroxymethyl-2-furyl)indazole and demonstrated an antiproliferative and platelet-inhibiting action. For various indazoles an inhibitory action on platelet aggregation is described in EP-A-667 345; heterocyclylmethyl-substituted and benzyl-substituted pyrazoles are furthermore described in WO-A-98/16 507 and WO-A-98/16 223. In international patent application PCT/EP99/05636, pyrimidines are described which show an sGC-stimulating activity.

Certain cycloalkano[d]pyrimidines and cyclopenta[d] pyrimidines are already known. Thus, in DE-A-40 29 654 fungicidally active 2-phenylcyclo-alkanopyrimidines are described which in the 4-position carry specific amino substituents which contain alkynyl groups. In U.S. Pat. No. 3,346,452 and U.S. Pat. No. 3,322,759, cycloalkanopyrimidines are described which carry an aminoalkylamino group in the 4-position and which have analgesic actions. In WO-A-97/47 601 specific bicyclic pyrimidines are described which act as dopamine receptor antagonists and can be employed, for example, for the treatment of schizophrenia and which carry a heterocyclylalkylamino substituent in which the heterocycle is bonded via a ring nitrogen atom. In JP-A-07/228 573, 2-phenylcycloalkanopyrimidines are described which are serotonin receptor antagonists and are suitable as psychopharmaceuticals and which carry a piperazino substituent or homopiperazino substituent in the 4-position. In EP-A-826 673 2-phenylcycloalkanopyrimidines are described which act on benzodiazepine receptors and have, for example, an anxiolytic action and which in the 4-position carry specific amino substituents which contain aminocarbonyl groups.

Surprisingly, it has now been found that the pyrimidines of the formula I according to the invention bring about strong guanylate cyclase activation, on account of which they are suitable for the therapy and prophylaxis of diseases which are associated with a low cGMP level.

The present invention thus relates to compounds of the formula I

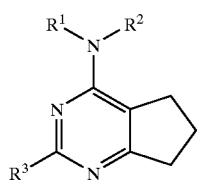

I in which $R^1$ and $R^2$, which are independent of one another and can be identical or different, are hydrogen, or $(C_1-C_8)$-alkyl which can be substituted by one or more identical or different substituents from the group consisting of hydroxyl, $(C_1-C_4)$-alkoxy, $(C_1-C_4)$-alkyl-S(O)$_m$—, phenyl, naphthyl and pyridyl, or $(C_3-C_9)$-cycloalkyl which can be substituted by one or more identical or different substituents from the group consisting of $(C_1-C_4)$-alkyl, hydroxyl, amino and benzyl, or the radical of a 5-membered to 7-membered saturated heterocyclic ring which contains one or two identical or different hetero ring members from the group consisting of O, $NR^{10}$ and $S(O)_m$ and which can be substituted by one or more identical or different substituents from the group consisting of $(C_1-C_4)$-alkyl, hydroxyl and aryl-$(C_1-C_4)$-alkyl, where radicals phenyl, naphthyl, pyridyl and benzyl contained in the radicals $R^1$ or $R^2$ can be unsubstituted or can be substituted in the aromatic ring by one or more identical or different substituents from the group consisting of halogen, $(C_1-C_4)$-alkyl, phenyl, $CF_3$, $NO_2$, OH, —O—$(C_1-C_4)$-alkyl, —O—$(C_2-C_4)$-alkyl—O—$(C_1-C_4)$-alkyl, $(C_1-C_2)$-alkylenedioxy, $NH_2$, —NH—$(C_1-C_4)$-alkyl, —N(($C_1-C_4$)-alkyl)$_2$, —NH—CHO, —NH—CO—$(C_1-C_4)$-alkyl, —CN, —CO—$NH_2$, —CO—NH—$(C_1-C_4)$-alkyl, —CO—N(($C_1-C_4$)-alkyl)$_2$, —CO—OH, —CO—O—$(C_1-C_4)$-alkyl, —CHO and —CO—$(C_1-C_4)$-alkyl, but where $R^1$ and $R^2$ cannot both simultaneously be hydrogen; or the radical $R^1R^2N$— is a radical, bonded via a ring nitrogen atom, of a 5-membered to 7-membered saturated heterocyclic ring which, in addition to the nitrogen atom carrying the radicals $R^1$ and $R^2$, can contain a further hetero ring member from the group consisting of O and $S(O)_m$ and which can be substituted by one or more identical or different substituents from the group consisting of $(C_1-C_4)$-alkyl, hydroxyl, $(C_1-C_4)$-alkoxy and $R^{11}R^{12}N$;

$R^3$ is aryl but cannot be unsubstituted phenyl;

$R^{10}$ is hydrogen, $(C_1-C_4)$-alkyl, aryl-$(C_1-C_4)$-alkyl-, hydroxy-$(C_1-C_4)$-alkyl-, hydroxycarbonyl-$(C_1-C_4)$-alkyl-, $((C_1-C_4)$-alkoxycarbonyl)-$(C_1-C_4)$-alkyl-, $R^{11}R^{12}N$—CO—$(C_1-C_4)$-alkyl-, $R^{13}$—$SO_2$— or aryl, $R^{11}$ and $R^{12}$ are identical or different radicals from the group consisting of hydrogen and $(C_1-C_4)$-alkyl;

$R^{13}$ is $(C_1-C_4)$-alkyl, aryl or $R^{11}R^{12}N$;

aryl is phenyl, naphthyl or heteroaryl, which can all be substituted by one or more identical or different substituents from the group consisting of halogen, $(C_1-C_4)$-alkyl, phenyl, $CF_3$, $NO_2$, OH, —O—$(C_1-C_4)$-alkyl, —O—$(C_2-C_4)$-alkyl-O—$(C_1-C_4)$-alkyl, $(C_1-C_2)$-alkylenedioxy, $NH_2$, —NH—$(C_1-C_4)$-alkyl, —N(($C_1-C_4$)-alkyl)$_2$, —NH—CHO, —NH—CO—$(C_1-C_4)$-alkyl, —CN, —CO—$NH_2$, —CO—NH—$(C_1-C_4)$-alkyl, —CO—N(($C_1-C_4$)-alkyl)$_2$, —CO—OH, —CO—O—$(C_1-C_4)$-alkyl, —CHO and —CO—$(C_1-C_4)$-alkyl;

heteroaryl is the radical of a monocyclic 5-membered or 6-membered aromatic heterocycle or of a bicyclic 8-membered to 10-membered aromatic heterocycle, each of which contain one or more identical or different ring heteroatoms from the group consisting of N, O and S;

m is 0, 1 or 2;

in all their stereoisomeric forms and mixtures thereof in all ratios, and their physiologically tolerable salts.

If groups or substituents can occur a number of times in the compounds of the formula I, they can all independently of one another have the indicated meanings and can each be identical or different.

Alkyl radicals can be straight-chain or branched. This also applies if they are contained in other groups, for example in alkoxy groups, alkoxycarbonyl groups or amino groups, or if they are substituted. Examples of alkyl groups are methyl, ethyl, propyl, butyl, pentyl, hexyl, heptyl, octyl, the n-isomers of these radicals, isopropyl, isobutyl, isopentyl, sec-butyl, tert-butyl, neopentyl, 3,3-dimethylbutyl. The term alkyl here is expressly also understood as meaning, in addition to saturated alkyl radicals, unsaturated alkyl radicals which contain one or more double bonds i.e. alkenyl radicals. Unsaturated alkyl radicals naturally contain at least two carbon atoms, unsaturated $(C_1-C8)$-alkyl radicals or $(C_1-C_4)$-alkyl radicals thus also comprise $(C_2-C_8)$-alkenyl radicals and $(C_2-C_4)$-alkenyl radicals. Examples of such unsaturated alkyl radicals are the vinyl radical, the 1-propenyl radical, the 2-propenyl radical (allyl radical), the 2-butenyl radical, the 2-methyl-2-propenyl radical or the 3-methyl-2-butenyl radical. If alkyl radicals are substituted by one or more substituents, they are preferably substituted by one, two or three, in particular by one or two, identical or different substituents. Substituents can be situated on any desired carbon atoms of the alkyl radical.

Cycloalkyl is, for example, cyclopropyl, cyclobutyl, cyclopentyl, cyclohexyl, cycloheptyl, cyclooctyl or cyclononyl, which can all also be substituted as indicated, for example by one or more identical identical or different $(C_1-C_4)$-alkyl radicals, in particular by methyl, and/or by hydroxyl. If cycloalkyl radicals are substituted by one or more substituents, they are preferably substituted by one, two, three or four, in particular by one or two, identical or different substituents. Examples of such substituted cycloalkyl radicals are 4-methylcyclohexyl, 4-tert-butylcyclohexyl, 4-hydroxycyclohexyl, 4-aminocyclohexyl or 2,3-dimethylcyclopentyl. Substituents can be situated on any desired carbon atoms of the cycloalkyl radical.

Carbocyclic aryl radicals such as phenyl radicals and naphthyl radicals and heteroaryl radicals can, if not stated otherwise, be unsubstituted or carry one or more, for example one, two, three or four, identical or different substituents, which can be situated in any desired positions. If not stated otherwise, the substituents indicated in the definition of the group aryl, for example, can occur as substituents in these radicals. If nitro groups are present as substituents in compounds of the formula I, preferably altogether only up to two nitro groups are present in the molecule. If an aryl radical such as, for example, a phenyl radical in turn carries a phenyl radical as a substituent, the benzene ring in the latter can also in turn be unsubstituted or substituted by one or more, for example one, two, three or four, identical or different radicals, for example by radicals from the group consisting of $(C_1–C_4)$-alkyl, halogen, hydroxyl, $(C_1–C_4)$-alkoxy, trifluoromethyl, cyano, hydroxycarbonyl, $((C_1–C_4)$-alkoxy)carbonyl, aminocarbonyl, nitro, amino, $(C_1–C_4)$-alkylamino, di-$((C_1–C_4)$-alkyl)amino and $((C_1–C_4)$-alkyl)carbonylamino.

In monosubstituted phenyl radicals, the substituent can be situated in the 2-position, the 3-position or the 4-position, in disubstituted phenyl radicals the substituents can be situated in the 2,3-position, 2,4-position, 2,5-position, 2,6-position, 3,4-position or 3,5-position. In trisubstituted phenyl radicals, the substituents can be situated in the 2,3,4-position, 2,3,5-position, 2,3,6-position, 2,4,5-position, 2,4,6-position or 3,4,5-position. Naphthyl can be 1-naphthyl or 2-naphthyl. In monosubstituted 1-naphthyl radicals, the substituent can be situated in the 2-position, the 3-position, the 4-position, the 5-position, the 6-position, the 7-position or the 8-position, in monosubstituted 2-naphthyl radicals in the 1-position, the 3-position, the 4-position, the 5-position, the 6-position, the 7-position or the 8-position. In polysubstituted naphthyl radicals, for example di- or trisubstituted naphthyl radicals, the substituents can also be situated in all possible positions.

If not stated otherwise, heteroaryl radicals, radicals of saturated heterocyclic rings and radicals of rings which are formed from two groups bonded to a nitrogen atom together with this nitrogen atom are preferably derived from heterocycles which contain one, two, three or four identical or different ring heteroatoms, particularly preferably from heterocycles which contain one or two or three, in particular one or two, identical or different heteroatoms. If not stated otherwise, the heterocycles can be monocyclic or polycyclic, for example monocyclic, bicyclic or tricyclic. Preferably, they are monocyclic or bicyclic, in particular monocyclic. The rings preferably contain 5, 6 or 7 ring members. Examples of monocyclic and bicyclic heterocyclic systems from which radicals occurring in the compounds of the formula I can be derived are pyrrole, furan, thiophene, imidazole, pyrazole, 1,2,3-triazole, 1,2,4-triazole, 1,3-dioxole, 1,3-oxazole, 1,2-oxazole, 1,3-thiazole, 1,2-thiazole, tetrazole, pyridine, pyridazine, pyrimidine, pyrazine, pyran, thiopyran, 1,4-dioxin, 1,2-oxazine, 1,3-oxazine, 1,4-oxazine, 1,2-thiazine, 1,3-thiazine, 1,4-thiazine, 1,2,3-triazine, 1,2,4-triazine, 1,3,5-triazine, 1,2,4,5-tetrazine, azepine, 1,2-diazepine, 1,3-diazepine, 1,4-diazepine, 1,3-oxazepine, 1,3-thiazepine, indole, benzothiophene, benzofuran, benzothiazole, benzimidazole, quinoline, isoquinoline, cinnoline, quinazoline, quinoxaline, phthalazine, thienothiophenes, 1,8-naphthyridine and other naphthyridines, pteridine, or phenothiazine, all in each case in saturated form (perhydro form) or in partially unsaturated form (for example dihydro form and tetrahydro form) or in maximally unsaturated form, if the forms concerned are known and stable. The heterocycles which are suitable also include, for example, the saturated heterocycles pyrrolidine, piperidine, perhydroazepine (hexamethyleneimine), piperazine, morpholine, 1,3-thiazolidine and thiomorpholine which—if this is in accord with the respective definition—are examples for radicals of saturated heterocyclic rings and for radicals of rings which are formed from two groups bonded to a nitrogen atom together with this nitrogen atom. The degree of saturation of heterocylic groups is indicated in the individual definitions. Unsaturated heterocycles can, for example, contain one, two or three double bonds in the ring, 5-membered rings and 6-membered rings in monocyclic and polycyclic heterocycles can, in particular, also be aromatic.

Heterocyclic radicals can be bonded via any suitable ring carbon atom. Nitrogen heterocycles, for example pyrrole, imidazole, pyrrolidine, piperidine, hexamethyleneimine, 1,3-thiazolidine, morpholine, thiomorpholine, piperazine etc., can also be bonded via any suitable ring nitrogen atom, in particular if the nitrogen heterocycle concerned is bonded to a carbon atom. For example, a thienyl radical can be present as a 2-thienyl radical or 3-thienyl radical, a furyl radical as a 2-furyl radical or 3-furyl radical, a piperidine radical as a 1-piperidinyl radical (=piperidino radical), 2-piperidinyl radical, 3-piperidinyl radical or 4-piperidinyl radical, a (thio)morpholine radical as a 2-(thio)morpholinyl radical, 3-(thio)morpholinyl radical or 4-(thio)morpholinyl radical (=(thio)morpholino radical). A radical which is derived from 1,3-thiazole can be bonded via the 2-position, the 3-position, the 4-position or the 5-position, a radical which is derived from imidazole can be bonded via the 1-position, the 2-position, the 4-position or the 5-position. A pyridyl radical can be a 2-pyridyl radical, 3-pyridyl radical or 4-pyridyl radical.

If not stated otherwise, the heterocyclic groups can be unsubstituted or can carry one or more, for example one, two, three or four, in particular one or two, identical or different substituents. The substituents in heterocycles can be situated in any desired positions, for example in a 2-thienyl radical or 2-furyl radical in the 3-position and/or in the 4-position and/or in the 5-position, in a 3-thienyl radical or 3-furyl radical in the 2-position and/or in the 4-position and/or in the 5-position, in a 2-pyridyl radical in the 3-position and/or in the 4-position and/or in the 5-position and/or in the 6-position, in a 3-pyridyl radical in the 2-position and/or in the 4-position and/or in the 5-position and/or in the 6-position, in a 4-pyridyl radical in the 2-position and/or in the 3-position and/or in the 5-position and/or in the 6-position. If not stated otherwise, the substituents which can occur are, for example, the substituents indicated in the definition of the group aryl, in the case of saturated or partially unsaturated heterocycles as further substituents also the oxo group and the thioxo group. Substituents on a heterocycle and also substituents on a carbocycle can also form a ring, further rings can thus be fused to a ring system such that, for example, cyclopenta-fused, cyclohexa-fused or benzo-fused rings can be present. If not stated otherwise, possible substituents on a substitutable nitrogen atom of a heterocycle are, for example, unsubstituted and substituted $(C_1–C_4)$-alkyl radicals, aryl radicals, acyl radicals such as —CO—$(C_1–C_4)$-alkyl or —CO-aryl, or sulfonyl radicals such as —$SO_2$—$(C_1–C_4)$-alkyl or —$SO_2$-aryl. Suitable sulfur heterocycles can also be present as S-oxides or S,S-dioxides, i.e. they can contain the group $S(=O)$ or the group $S(=O)_2$ instead of a sulfur atom. Suitable nitrogen atoms in the compounds of the formula I can also be present as N-oxides or as quaternary salts with an anion derived from a physiologically tolerable acid as a counterion. Pyridyl radicals can be present, for example, as pyridine N-oxides.

Halogen is fluorine, chlorine, bromine or iodine, preferably fluorine or chlorine.

The present invention includes all stereoisomeric forms of the compounds of the formula I. Asymmetric centers contained in the compounds of the formula I can all independently of one another have the S configuration or the R configuration. The invention includes all possible enantiomers and diastereomers, as well as mixtures of two or more stereoisomeric forms, for example mixtures of enantiomers and/or diastereomers, in all ratios. The invention thus relates to enantiomers in enantiomerically pure form, both as levorotatory and as dextrorotatory antipodes, in the form of racemates and in the form of mixtures of the two enantiomers in all ratios. In the presence of cis/trans isomerism, for example on cycloalkyl groups, the invention relates both to the cis form and the trans form and mixtures of these forms in all ratios. Individual stereoisomers can be prepared, if desired, by resolution of a mixture by customary methods, for example by chromatography or crystallization, by use of stereochemically homogeneous starting substances in the synthesis or by stereoselective synthesis. If appropriate, derivatization can be carried out before separation of stereoisomers. The separation of a stereoisomer mixture can be carried out at the stage of the compounds of the formula I or at the stage of an intermediate in the course of the synthesis. If mobile hydrogen atoms are present, the present invention also includes all tautomeric forms of the compounds of the formula I.

If the compounds of the formula I contain one or more acidic or basic groups, the invention also relates to the corresponding physiologically or toxicologically tolerable salts, in particular the pharmaceutically utilizable salts. Thus the compounds of the formula I which contain acidic groups can be present on these groups, and can be used according to the invention, for example, as alkali metal salts, alkaline earth metal salts or as ammonium salts. Examples of such salts are sodium salts, potassium salts, calcium salts, magnesium salts, salts with ammonia or organic amines, for example ethylamine, ethanolamine, triethanolamine or amino acids, or salts which contain quaternary organic ammonium ions as cation. Compounds of the formula I which contain one or more basic, i.e. protonatable, groups can be present, and can be used according to the invention, in the form of their acid addition salts with physiologically tolerable inorganic or organic acids, for example as salts with hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfamic acid, phenylpropionic acid, gluconic acid, ascorbic acid, isonicotinic acid, citric acid, adipic acid etc. If the compounds of the formula I simultaneously contain acidic and basic groups in the molecule, in addition to the salt forms outlined the invention also includes internal salts or betaines (zwitterions). Salts can be obtained from the compounds of the formula I by customary processes known to the person skilled in the art, for example by combination with an organic or inorganic acid or base in a solvent or dispersant, or alternatively from other salts by anion exchange or cation exchange. The present invention also includes all salts of the compounds of the formula I which, because of low physiological tolerability, are not directly suitable for use in pharmaceuticals, but are suitable, for example, as intermediates for chemical reactions or for the preparation of physiologically tolerable salts.

The present invention furthermore includes all solvates of compounds of the formula I, for example hydrates or adducts with alcohols, and also derivatives of the compounds of the formula I such as, for example, esters, and prodrugs and active metabolites.

Preferably, one of the radicals $R^1$ and $R^2$ is $(C_1–C_8)$-alkyl which can be substituted by one or more identical or different substituents from the group consisting of hydroxyl, $(C_1–C_4)$-alkoxy, $(C_1–C_4)$-alkyl-$S(O)_m$—, unsubstituted or substituted phenyl and unsubstituted or substituted naphthyl, or $(C_3–C_9)$-cycloalkyl which can be substituted by one or more identical or different substituents from the group consisting of $(C_1–C_4)$-alkyl, hydroxyl, amino and unsubstituted or substituted benzyl. Particularly preferably, the other of the radicals $R^1$ and $R^2$ is hydrogen, $(C_1–C_8)$-alkyl which can be substituted by one or more identical or different substituents from the group consisting of hydroxyl, $(C_1–C_4)$-alkoxy, $(C_1–C_4)$-alkyl-$S(O)_m$—, unsubstituted or substituted phenyl and unsubstituted or substituted naphthyl, or $(C_3–C_9)$-cycloalkyl which can be substituted by one or more identical or different substituents from the group consisting of $(C_1–C_4)$-alkyl, hydroxyl, amino and unsubstituted or substituted benzyl. It is very particularly preferred if one of the radicals $R^1$ and $R^2$ is $(C_1–C_8)$-alkyl or $(C_3–C_9)$-cycloalkyl and the other of the radicals $R^1$ and $R^2$ is hydrogen or if the radicals $R^1$ and $R^2$ are identical or different $(C_1–C_8)$-alkyl, where all alkyl radicals and cycloalkyl radicals can be unsubstituted or substituted as indicated. It is especially preferred if one of the radicals $R^1$ and $R^2$ is $(C_3–C_9)$-cycloalkyl which can be substituted by one or more identical or different substituents from the group consisting of $(C_1–C_4)$-alkyl, hydroxyl, amino and unsubstituted or substituted benzyl, and the other of the radicals $R^1$ and $R^2$ is hydrogen. If one of the radicals $R^1$ and $R^2$ is $(C_3–C_9)$-cycloalkyl which can be substituted by one or more identical or different substituents from the group consisting of $(C_1–C_4)$-alkyl, hydroxyl, amino and unsubstituted or substituted benzyl, or the radical of a 5-membered to 7-membered saturated heterocyclic ring which contains one or two identical or different hetero ring members from the group consisting of O, $NR^{10}$ and $S(O)_m$ and which can be substituted by one or more identical or different substituents from the group consisting of $(C_1–C_4)$-alkyl, hydroxyl and aryl-$(C_1–C_4)$-alkyl-, then the other of the radicals $R^1$ and $R^2$ is preferably hydrogen.

An alkyl radical representing $R^1$ or $R^2$ is preferably an unsubstituted or substituted $(C_1–C_4)$-alkyl radical. A $(C_3–C_9)$-cycloalkyl radical representing $R^1$ or $R^2$ is preferably an unsubstituted or substituted radical from the group consisting of cyclopropyl, cyclobutyl, cyclopentyl, cyclohexyl and cycloheptyl, in particular unsubstituted or substituted cyclopentyl or cyclohexyl. Preferably, a substituted cycloalkyl radical representing $R^1$ or $R^2$ is substituted by one or more radicals from the group consisting of $(C_1–C_4)$-alkyl, hydroxyl and amino, particularly preferably by one or more $(C_1–C_4)$-alkyl radicals or by a hydroxyl group or by an amino group, in particular by a hydroxyl group. A radical of a 5-membered to 7-membered saturated heterocyclic ring representing $R^1$ or $R^2$ preferably contains a hetero ring member from the group consisting of O, $NR^{10}$ and $S(O)_m$, particularly preferably a group $NR^{10}$ as a hetero ring member. Preferably, a heterocyclic ring of this type is bonded via a ring carbon atom which is not bonded directly to a hetero ring member. Examples of radicals of heterocyclic rings of this type are optionally substituted pyrrolidinyl, for example 3-pyrrolidinyl, optionally substituted piperidinyl, for example 3-piperidinyl or 4-piperidinyl, tetrahydrofuryl, for example 3-tetrahydrofuryl, tetrahydrothienyl and its S-oxides and S,S-dioxides, for example 3-tetrahydrothienyl, or tetrahydro(thio)pyranyl.

In addition to the abovementioned preferred meanings of $R^1$ and $R^2$, it is furthermore preferred if the group $R^1R^2N$ is a radical, bonded via a ring nitrogen atom, of a 5-membered, 6-membered or 7-membered saturated heterocyclic ring which, in addition to the nitrogen atom carrying the radicals $R^1$ and $R^2$, can additionally contain as a further hetero ring member an oxygen atom or a group $S(O)_m$ and which can be substituted by one or more identical or different substituents from the group consisting of $(C_1-C_4)$-alkyl, hydroxyl, $(C_1-C_4)$-alkoxy and $R^{11}R^{12}N$. A radical of a heterocyclic ring representing $R^1R^2N$ is preferably derived from a 5-membered or 6-membered saturated heterocyclic ring, particularly preferably from piperidine, morpholine or thiomorpholine (and its S-oxide and S,S-dioxide), which can be substituted as indicated, very particularly preferably from unsubstituted piperidine, morpholine or thiomorpholine (and its S-oxide and S,S-dioxide).

The aryl group representing $R^3$ is preferably substituted phenyl, very particularly preferably phenyl which is substituted by one or two of the substituents indicated above in the definition of aryl. Especially preferably, $R^3$ is phenyl which is substituted by one or two substituents from the group consisting of halogen and $(C_1-C_4)$-alkyl, moreover preferably phenyl which is substituted by chlorine or methyl. The substituent in a monosubstituted phenyl group representing $R^3$ is preferably in the para-position.

Aryl is preferably phenyl or 5-membered or 6-membered monocyclic heteroaryl having one or two, in particular one, heteroatom from the group consisting of N, O and S, which can be substituted as indicated, particularly preferably unsubstituted or substituted phenyl or unsubstituted pyridyl, thienyl or furyl, very particularly preferably unsubstituted or substituted phenyl or unsubstituted pyridyl.

Preferred compounds of the formula I are those in which one or more of the radicals contained therein have preferred meanings, the present invention relating to all combinations of preferred substituent definitions and specific preferred substituent definitions. The present invention also includes, of all preferred compounds of the formula I, all their stereoisomeric forms and mixtures thereof in all ratios, and their physiologically tolerable salts.

The present invention also relates to processes for the preparation of the compounds of the formula I, which are explained below and by which the compounds according to the invention are obtainable. The compounds of the formula I can be prepared by first reacting an amidine of the formula II in a manner known per se with a 2-oxocyclopentanecarboxylic acid ester of the formula III to give a 4-hydroxycyclopentapyrimidine of the formula IV. R in the formula III is, for example, $(C_1-C_4)$-alkyl such as methyl or ethyl. The hydroxy-cyclopentapyrimidine of the formula IV is then activated, for example by conversion into a 4-halocyclopentapyrimidine. For example, the compound of the formula IV can be converted into the 4-chlorocyclopentapyrimidine of the formula V by reaction with a phosphorus halide such as phosphorus oxychloride. By reaction of the compound of the formula V (or of another reactive derivative of the hydroxycyclopentapyrimidine) with the desired amine of the formula VI, the compound of the formula I according to the invention is then obtained with replacement of the chlorine by the amino group. Suitable solvents for this replacement reaction are, for example, water, alcohols such as methanol, ethanol or isopropanol, ethers such as tetrahydrofuran or dioxane, amides such as dimethylformamide (DMF) or N-methylpyrrolidone (NMP), or hydrocarbons or halogenated hydrocarbons such. as benzene, toluene, xylene, chlorobenzene or dichlorobenzene.

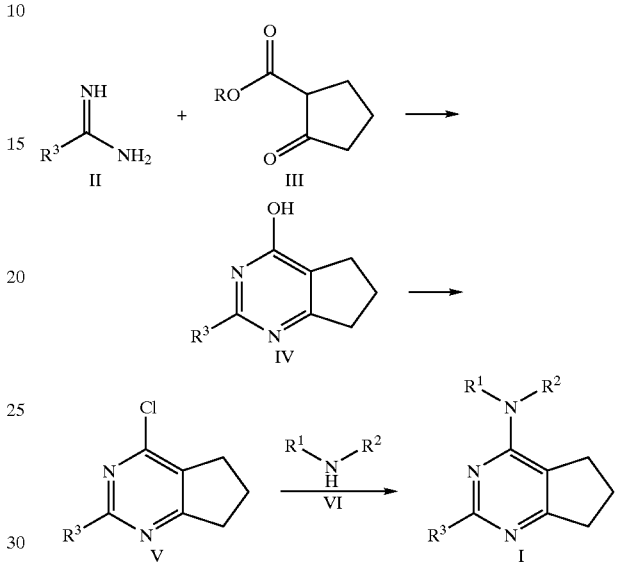

These reactions can be carried out in a wide temperature range. Reaction temperatures of 20° C. to 150° C. are preferred. They can be accelerated by addition of suitable bases such as, for example, sodium bicarbonate, sodium carbonate, potassium carbonate, sodium alkoxides, triethylamine or pyridine, in the first and in the last step additionally also by excess amidine or amine. Instead of the free amidines of the formula II, the corresponding amidinium salts can also be employed. In this case, it is particularly convenient to carry out the first step with addition of bases. The intermediates of the formulae IV and V and the final compounds of the formula I can be separated from the respective reaction mixture by customary processes such as crystallization, sublimation, chromatography or distillation and, if desired, purified, but, depending on the circumstances of the individual case, the intermediates can also be reacted further without isolation. Moreover, in the compounds of the formula I thus obtained functional groups can be converted. For example, thioether groups can be converted into sulfones or sulfoxides by oxidation with a peroxy compound such as 3-chloroperbenzoic acid or monoperoxyphthalic acid or hydrogen peroxide, or carboxylic acid ester groups can be hydrolyzed to the carboxylic acids.

All reactions for the synthesis of the compounds of the formula I are well known per se to the person skilled in the art and can be carried out under standard conditions according to or analogously to literature procedures, such as are described, for example, in Houben-Weyl, Methoden der Organischen Chemie [Methods of Organic Chemistry], Thieme-Verlag, Stuttgart, or Organic Reactions, John Wiley & Sons, New York. Depending on the conditions of the individual case, it may also be advantageous or necessary for the avoidance of side reactions in the synthesis of the compounds of the formula I to temporarily block certain functional groups by the introduction of protective groups and then later to liberate them again or to employ functional groups first in the form of precursors, from which the desired functional group is then produced in a later step. Such synthesis strategies and the protective groups or precursors suitable for the individual case are known to the person skilled in the art. The starting amidines of the formula II or their salts, the oxoesters of the formula III and the amines of the formula VI are commercially obtainable or can be prepared by or analogously to known processes.

The compounds of the formula I according to the invention bring about an increase in the cGMP concentration by means of the activation of soluble guanylate cyclase (sGC) and are therefore valuable agents for the therapy and prophylaxis of diseases which are associated with a low or reduced cGMP level or are caused by such a level or for whose therapy or prophylaxis an increase in the cGMP level present is desired. The activation of sGC by the compounds of the formula I can be investigated, for example, in the activity assay described below. Preferred substances of the formula I are those which show an at least threefold activation in this assay.

Diseases and pathological conditions which are associated with a low cGMP level or in which an increase in the cGMP level is desired and for whose therapy and prophylaxis compounds of the formula I can be employed are, for example, cardiovascular disorders such as endothelial dysfunction, diastolic dysfunction, atherosclerosis, high blood pressure, stable and unstable angina pectoris, thromboses, restenoses, myocardial infarct, strokes, cardiac insufficiency or pulmonary hypertension, or, for example, erectile dysfunction, bronchial asthma, chronic renal insufficiency and diabetes. Compounds of the formula I can moreover be employed in the therapy of liver cirrhosis and for improving restricted learning capacity or memory power.

The compounds of the formula I and their physiologically tolerable salts can thus be used in animals, preferably in mammals, and in particular in humans, as pharmaceuticals on their own, in mixtures with one another or in the form of pharmaceutical preparations. The present invention therefore also relates to the compounds of the formula I and their physiologically tolerable salts for use as pharmaceuticals, their use for the normalization of a disturbed cGMP balance and in particular their use in the therapy and prophylaxis of the abovementioned syndromes, and their use for the production of medicaments therefor. The present invention furthermore relates to pharmaceutical preparations which contain an efficacious dose of at least one compound of the formula I and/or of a physiologically tolerable salt thereof as an active constituent and a pharmaceutically tolerable carrier, that is one or more pharmaceutically tolerable vehicles and/or additives (or excipients).

The pharmaceuticals according to the invention can be administered orally, for example in the form of pills, tablets, film-coated tablets, coated tablets, granules, hard and soft gelatin capsules, aqueous, alcoholic or oily solutions, syrups, emulsions or suspensions, or rectally, for example in the form of suppositories. Administration, however, can also be carried out parenterally, for example subcutaneously, intramuscularly or intravenously in the form of injection solutions or infusion solutions. Further possible administration forms are, for example, percutaneous or topical application, for example in the form of ointments, tinctures, sprays or transdermal therapeutic systems, or administration by inhalation in the form of nasal sprays or aerosol mixtures, or, for example, microcapsules, implants or rods. The preferred administration form depends, for example, on the disease to be treated and its severity.

The pharmaceutical preparations normally contain approximately 0.1 to 1000 mg, preferably 0.2 to 500 mg, in particular 1 to 200 mg, of active compound of the formula I and/or its physiologically tolerable salts and one or more pharmaceutically innocuous vehicles and/or additives. Depending on the type of pharmaceutical preparation, however, also a larger amount of active compound can be present. The pharmaceutical preparations can be produced in a manner known per se. For this, one or more compounds of the formula I and/or their physiologically tolerable salts are brought, together with one or more solid or liquid pharmaceutical vehicles and/or additives and, if desired, in combination with other pharmaceutical active compounds having therapeutic or prophylactic action, into a suitable administration form or dosage form, which can then be used as a pharmaceutical in human or veterinary medicine. The pharmaceutical preparations normally contain 0.5 to 90 percent by weight of the compounds of the formula I and/or their physiologically tolerable salts.

For the production, for example, of pills, tablets, coated tablets and hard gelatin capsules, it is possible to use lactose, starch, for example corn starch, or starch derivatives, talc, stearic acid or its salts, etc. Vehicles for soft gelatin capsules and suppositories are, for example, fats, waxes, semisolid and liquid polyols, natural or hardened oils etc. Suitable vehicles for the preparation of solutions, for example injection solutions, or of emulsions or syrups are, for example, water, physiological saline solution, alcohols such as ethanol, glycerol, polyols, sucrose, invert sugar, glucose, mannitol, vegetable oils etc. The compounds of the formula I and their physiologically tolerable salts can also be lyophilized and the lyophilizates obtained used, for example, for the production of injection preparations or infusion preparations. Suitable vehicles for microcapsules, implants or rods are, for example, copolymers of glycolic acid and lactic acid.

In addition to the active compounds and vehicles, the pharmaceutical preparations can additionally contain customary additives, for example fillers, disintegrants, binders, lubricants, wetting agents, stabilizers, emulsifiers, dispersants, preservatives, sweetening agents, colorants, flavorings, aromatizers, thickening agents, diluents, buffer substances, solvents, solubilizers, agents for achieving a depot effect, salts for altering the osmotic pressure, coating agents or antioxidants.

The dose of the active compound of the formula I and/or its physiologically tolerable salts which is to be administered depends on the individual case and is to be adapted to the individual conditions as is customary for an optimal action. Thus it depends on the nature and severity of the disease to be treated, on the sex, age, weight and individual responsiveness of the human or animal to be treated, on the potency and duration of action of the compounds employed, on whether the therapy is acute or chronic or prophylaxis is carried out, or on whether further active compounds are administered in addition to compounds of the formula I. In general, a daily dose of approximately 0.01 to 100 mg/kg, preferably 0.1 to 10 mg/kg, in particular 0.3 to 5 mg/kg (in each case mg per kg of body weight) is appropriate in the case of administration to an adult of about 75 kg in weight to achieve the desired action. The daily dose can be administered in a single dose or, in particular in the case of administration of relatively large amounts, divided into a number of, for example two, three or four, individual doses. If appropriate, depending on individual behavior, it may be necessary to deviate upward or downward from the daily dose indicated.

The compounds of the formula I activate the soluble guanylate cyclase. On account of this property, apart from as pharmaceutical active compounds in human medicine and veterinary medicine, they can also be used as a scientific tool or as an aid for biochemical investigations in which an effect on guanylate cyclase of this type is intended, and also for diagnostic properties, for example in the in vitro diagnosis of cell or tissue samples. In addition, the compounds of the formula I and their salts, as already mentioned above, can serve as intermediates for the preparation of further pharmaceutical active compounds.

The following examples illustrate the invention without restricting it.

EXAMPLES

Example 1
2-(4-Chlorophenyl)-4-hydroxy-6,7-dihydro-5H-cyclopenta[d]pyrimidine 7.1 g of methyl 2-oxocyclopentane-1-carboxylate and 9.6 g of 4-chlorobenz-amidine hydrochloride were introduced into 50 ml of methanol. 5.6 g of potassium tert-butoxide were added with stirring. The reaction mixture was stirred under reflux for 4 hours and then poured onto ice water. The crystalline product was filtered off with suction, washed with water and recrystallized from dimethylformamide. Yield: 8.8 g. M.p.: 282° C.

The following were prepared analogously:

Example 2
2-(3-Chlorophenyl)-4-hydroxy-6,7-dihydro-5H-cyclopenta[d]pyrimidine; m.p.: 255° C.

Example 3
2-(4-Methoxyphenyl)-4-hydroxy-6,7-dihydro-5H-cyclopenta[d]pyrimidine; m.p.: 251° C.

Example 4
2-(3,4-Dimethoxyphenyl)-4-hydroxy-6,7-dihydro-5H-cyclopenta[d]pyrimidine; m.p.: 283° C.

Example 5
2-(3,5-Dichlorophenyl)-4-hydroxy-6,7-dihydro-5H-cyclopenta[d]pyrimidine; m.p.: 297° C.

Example 6
2-(4-Aminocarbonylphenyl)-4-hydroxy-6,7-dihydro-5H-cyclopenta[d]pyrimidine; m.p.: >300° C.

Example 7
2-(4-Methylphenyl)-4-hydroxy-6,7-dihydro-5H-cyclopenta[d]pyrimidine; m.p.: 273° C.

Example 8
2-(4-Chlorophenyl)-4-chloro-6,7-dihydro-5H-cyclopenta[d]pyrimidine 8.0 g of 2-(4-chlorophenyl)-4-hydroxy-6,7-dihydro-5H-cyclopenta[d]pyrimidine are heated to 100° C. in 10 ml of phosphorus oxychloride. After 3 hours, the cooled solution was cautiously poured onto ice water. The crystalline product was filtered off with suction, washed well with water and dried in vacuo at room temperature. Yield: 6.5 g. M.p.: 1450° C.

The following were prepared analogously:

Example 9
2-(3-Chlorophenyl)-4-chloro-6,7-dihydro-5H-cyclopenta[d]pyrimidine; m.p.: 138° C.

Example 10
2-(3,5-Dichlorophenyl)-4-chloro-6,7-dihydro-5H-cyclopenta[d]pyrimidine; m.p.: 165° C.

Example 11
2-(4-Methoxyphenyl)-4-chloro-6,7-dihydro-5H-cyclopenta[d]pyrimidine; m.p.: 109° C.

Example 12
2-(3,4-Dimethoxyphenyl)-4-chloro-6,7-dihydro-5H-cyclopenta[d]pyrimidine; m.p.: 152° C.

Example 13
2-(4-Methylphenyl)-4-chloro-6,7-dihydro-5H-cyclopenta[d]pyrimidine; m.p.: 162° C.

Example 14
2-(4-Cyanophenyl)-4-chloro-6,7-dihydro-5H-cyclopenta[d]pyrimidine The compound was obtained analogously to Example 8 starting from 2-(4-aminocarbonylphenyl)-4-hydroxy-6,7-dihydro-5H-cyclopenta[d]pyrimidine. M.p.: 201° C.

Example 15
2-(4-Chlorophenyl)-4-cyclopentylamino-6,7-dihydro-5H-cyclopenta[d]pyrimidine 0.265 g of 2-(4-chlorophenyl)-4-chloro-6,7-dihydro-5H-cyclopenta[d]pyrimidine, 0.4 g of cyclopentylamine and 1 ml of N-methylpyrrolidone were heated to 130° C. in an oil bath. After 5 hours, the mixture was diluted with 20 ml of water and stirred at room temperature. The precipitated product was filtered off with suction, washed with water and dried in vacuo at 40° C. Yield: 0.26 g. M.p.: 167° C.

Example 16
2-(3,5-Dichlorophenyl)-4-(trans-4-hydroxycyclohexylamino)-6,7-dihydro-5H-cyclopenta[d]pyrimidine methanesulfonic acid salt 0.15 g of 2-(3,5-dichlorophenyl)-4-chloro-6,7-dihydro-5H-cyclopenta[d]-pyrimidine, 0.39 g of trans-4-aminocyclohexanol hydrochloride, 0.18 g of potassium tert-butoxide and 1.5 ml of N-methylpyrrolidone were heated in an oil bath at 130° C. for 2 hours. 15 ml of water were added to the cooled solution and the precipitated product was filtered off with suction. The dried solid was taken up in 8 ml of ethyl acetate and 2 ml of isopropanol and treated with methanesulfonic acid. The precipitated product was filtered off with suction, washed with ethyl acetate and dried in vacuo at 40° C. Yield: 0.12 g. M.p.: 218° C.

The following compounds of the formula I were prepared analogously to Examples 15 and 16:

Example 17
2-(4-Chlorophenyl)-4-(N-benzylpiperidin-4-ylamino)-6,7-dihydro-5H-cyclopenta[d]pyrimidine dihydrochloride; m.p.: 275° C.

Example 18
2-(4-Chlorophenyl)-4-(2-hydroxyethylamino)-6,7-dihydro-5H-cyclopenta[d]-pyrimidine; m.p.: 160° C.

Example 19
2-(4-Chlorophenyl)-4-((3-pyridylmethyl)amino)-6,7-dihydro-5H-cyclopenta[d]-pyrimidine; m.p.: 209° C.

Example 20
2-(3-Chlorophenyl)-4-morpholino-6,7-dihydro-5H-cyclopenta[d]pyrimidine; m.p.: 132° C.

Example 21
2-(3-Chlorophenyl)-4-(2-hydroxyethylamino)-6,7-dihydro-5H-cyclopenta[d]-pyrimidine; m.p.: 150° C.

Example 22
2-(3-Chlorophenyl)-4-((3-pyridylmethyl)amino)-6,7-dihydro-5H-cyclopenta[d]-pyrimidine; m.p.: 185° C.

Example 23
2-(3-Chlorophenyl)-4-(2-(3-methoxyphenyl)ethylamino)-6,7-dihydro-5H-cyclopenta[d]pyrimidine hydrochloride; m.p.: 192° C.

Example 24
2-(4-Chlorophenyl)-4-thiomorpholino-6,7-dihydro-5H-cyclopenta[d]pyrimidine; m.p.: 159° C.

Example 25
2-(3-Chlorophenyl)-4-diethylamino-6,7-dihydro-5H-cyclopenta[d]pyrimidine hydrochloride; m.p.: 185° C.

Example 26
2-(4-Chlorophenyl)-4-diethylamino-6,7-dihydro-5H-cyclopenta[d]pyrimidine hydrochloride; m.p.: 185° C.

Example 27
2-(4-Chlorophenyl)-4-(2-(3-methoxyphenyl)ethylamino)-6,7-dihydro-5H-cyclopenta[d]pyrimidine hydrochloride; m.p.: 230° C.

Example 28
2-(4-Chlorophenyl)-4-(2-methoxyethylamino)-6,7-dihydro-5H-cyclopenta[d]-pyrimidine hydrochloride; m.p.: 208° C.

Example 29
2-(4-Chlorophenyl)-4-isobutylamino-6,7-dihydro-5H-cyclopenta[d]pyrimidine; m.p.: 121° C.

Example 30
2-(4-Chlorophenyl)-4-butylamino-6,7-dihydro-5H-cyclopenta[d]pyrimidine; m.p.: 121° C.

Example 31
2-(3-Chlorophenyl)-4-(2,2,6,6-tetramethylpiperidin-4-ylamino)-6,7-dihydro-5H-cyclopenta[d]pyrimidine; m.p.: 182° C.

Example 32
2-(3-Chlorophenyl)-4-cyclopentylamino-6,7-dihydro-5H-cyclopenta[d]pyrimidine; m.p.: 129° C.

Example 33
2-(3-Chlorophenyl)-4-butylamino-6,7-dihydro-5H-cyclopenta[d]pyrimidine; m.p.: oil.

Example 34
2-(4-Chlorophenyl)-4-(trans-4-hydroxycyclohexylamino)-6,7-dihydro-5H-cyclopenta[d]pyrimidine; m.p.: 216° C.

Example 35
2-(4-Chlorophenyl)-4-dipropylamino-6,7-dihydro-5H-cyclopenta[d]pyrimidine; m.p.: 114° C.

Example 36
2-(3-Chlorophenyl)-4-pyrrolidino-6,7-dihydro-5H-cyclopenta[d]pyrimidine; m.p.: 150° C.

Example 37
2-(3-Chlorophenyl)-4-hexamethyleneimino-6,7-dihydro-5H-cyclopenta[d]-pyrimidine hydrochloride; m.p.: resin.

Example 38
2-(3-Chlorophenyl)-4-thiomorpholino-6,7-dihydro-5H-cyclopenta[d]pyrimidine; m.p.: 134° C.

Example 39
2-(4-Methylphenyl)-4-(2-hydroxyethylamino)-6,7-dihydro-5H-cyclopenta[d]-pyrimidine; m.p.: 191° C.

Example 40
2-(4-Methylphenyl)-4-butylamino-6,7-dihydro-5H-cyclopenta[d]pyrimidine; m.p.: 133° C.

Example 41
2-(4-Methylphenyl)-4-cyclopentylamino-6,7-dihydro-5H-cyclopenta[d]pyrimidine; m.p.: 183° C.

Example 42
2-(4-Methylphenyl)-4-cyclohexylamino-6,7-dihydro-5H-cyclopenta[d]pyrimidine; m.p.: 163° C.

Example 43
2-(4-Methylphenyl)-4-(trans-4-hydroxycyclohexylamino)-6,7-dihydro-5H-cyclopenta[d]-pyrimidine; m.p.: 191° C.

Example 44
2-(4-Methylphenyl)-4-((3-pyridylmethyl)amino-6,7-dihydro-5H-cyclopenta[d]-pyrimidine; m.p.: 225° C.

Example 45
2-(4-Methylphenyl)-4-dipropylamino-6,7-dihydro-5H-cyclopenta[d]pyrimidine; m.p.: 117° C.

Example 46
2-(4-Methylphenyl)-4-pyrrolidino-6,7-dihydro-5H-cyclopenta[d]pyrimidine; m.p.: 203° C.

Example 47
2-(4-Methylphenyl)-4-thiomorpholino-6,7-dihydro-5H-cyclopenta[d]pyrimidine; m.p.: 160° C.

Example 48
2-(3,5-Dichlorophenyl)-4-(4-hydroxybutylamino)-6,7-dihydro-5H-cyclopenta[d]-pyrimidine; m.p.: 142° C.

Example 49
2-(3,5-Dichlorophenyl)-4-butylamino-6,7-dihydro-5H-cyclopenta[d]pyrimidine; m.p.: 93° C.

Example 50
2-(3,5-Dichlorophenyl)-4-cyclopentylamino-6,7-dihydro-5H-cyclopenta[d]-pyrimidine; m.p.: 153° C.

Example 51
2-(3,5-Dichlorophenyl)-4-((3-pyridylmethyl)amino)-6,7-dihydro-5-cyclopenta[d]-pyrimidine; m.p.: 207° C.

Example 52
2-(3,5-Dichlorophenyl)-4-dipropylamino-6,7-dihydro-5H-cyclopenta[d]pyrimidine; m.p.: 120° C.

Example 53
2-(3,5-Dichlorophenyl)-4-piperidino-6,7-dihydro-5H-cyclopenta[d]pyrimidine; m.p.: 147° C.

Example 54
2-(4-Methoxyphenyl)-4-(3-hydroxypropylamino)-6,7-dihydro-5H-cyclopenta[d]-pyrimidine; m.p.: 165° C.

Example 55
2-(4-Methoxyphenyl)-4-butylamino-6,7-dihydro-5H-cyclopenta[d]pyrimidine; m.p.: 119° C.

Example 56
2-(4-Methoxyphenyl)-4-cyclopentylamino-6,7-dihydro-5H-cyclopenta[d]-pyrimidine; m.p.: 154° C.

Example 57
2-(4-Methoxyphenyl)-4-cyclohexylamino-6,7-dihydro-5H-cyclopenta[d]-pyrimidine; m.p.: 138° C.

Example 58
2-(4-Methoxyphenyl)-4-(2-(2-chlorophenyl)ethylamino)-6,7-dihydro-5H-cyclopenta[d]pyrimidine; m.p.: 145° C.

Example 59
2-(4-Methoxyphenyl)-4-dipropylamino-6,7-dihydro-5H-cyclopenta[d]pyrimidine; m.p.: 74° C.

Example 60
2-(4-Methoxyphenyl)-4-hexamethyleneimino-6,7-dihydro-5H-cyclopenta[d]-pyrimidine; m.p.: 99° C.

Example 61
2-(4-Methoxyphenyl)-4-morpholino-6,7-dihydro-5H-cyclopenta[d]pyrimidine; m.p.: 192° C.

Example 62
2-(3,4-Dimethoxyphenyl)-4-(3-methoxypropylamino)-6,7-dihydro-5H-cyclopenta-[d]pyrimidine; m.p.: 107° C.

Example 63
2-(3,4-Dimethoxyphenyl)-4-cyclopentylamino-6,7-dihydro-5H-cyclopenta[d]-pyrimidine; m.p.: 138° C.

Example 64
2-(3,4-Dimethoxyphenyl)-4-cyclohexylamino-6,7-dihydro-5H-cyclopenta[d]-pyrimidine; m.p.: 70° C.

Example 65
2-(3,4-Dimethoxyphenyl)-4-butylamino-6,7-dihydro-5H-cyclopenta[d]pyrimidine; m.p.: 115° C.

Example 66
2-(3,4-Dimethoxyphenyl)-4-dipropylamino-6,7-dihydro-5H-cyclopenta[d]-pyrimidine; m.p.: 107° C.

Example 67
2-(3,4-Dimethoxyphenyl)-4-(2,6-dimethylmorpholino)-6,7-dihydro-5H-cyclopenta[d]pyrimidine; m.p.: 142° C.

Example 68
2-(3,4-Dimethoxyphenyl)-4-(di-(2-hydroxyethyl)amino)-6,7-dihydro-5H-cyclopenta[d]pyrimidine; m.p.: 115° C.

Example 69
2-(4-Cyanophenyl)-4-(3-methoxypropylamino)-6,7-dihydro-5H-cyclopenta[d]-pyrimidine; m.p.: 130° C.

Example 70
2-(4-Cyanophenyl)-4-benzylamino-6,7-dihydro-5H-cyclopenta[d]pyrimidine; m.p.: 168° C.

Example 71
2-(4-Cyanophenyl)-4-diethylamino-6,7-dihydro-5H-cyclopenta[d]pyrimidine; m.p.: 130° C.

Example 72
2-(4-Cyanophenyl)-4-piperidino-6,7-dihydro-5H-cyclopenta[d]pyrimidine; m.p.: 152° C.

Example 73
2-(4-Cyanophenyl)-4-morpholino-6,7-dihydro-5H-cyclopenta[d]pyrimidine; m.p.: 247° C.

Example 74
2-(4-Cyanophenyl)-4-((3-pyridylmethyl)amino)-6,7-dihydro-5H-cyclopenta[d]-pyrimidine; m.p.: 219° C.

Pharmacological Investigations

Activation of Soluble Guanylate Cyclase

The activation of soluble guanylate cyclase (sGC), which catalyzes the conversion of guanosine triphosphate (GTP) to cyclic guanosine monophosphate (cGMP) and pyrophosphate, by the compounds according to the invention was quantified with the aid of an enzyme immunoassay (EIA) from Amersham. For this, the test substances were first incubated with sGC in microtiter plates and then the quantity of the resulting cGMP was determined.

The sGC employed had been isolated from bovine lung (see Methods in Enzymology, Volume 195, p. 377). The test solutions (100 μl per well) contained 50 mM triethanolamine (TEA) buffer (pH 7.5), 3 mM $MgCl_2$, 3 mM reduced glutathione (GSH), 0.1 mM GTP, 1 mM 3-isobutyl-1-methylxanthine (IBMX), suitably diluted enzyme solution and the test substance or, in the control experiments, solvent. The test substances were dissolved in dimethyl sulfoxide (DMSO) and the solution was diluted with DMSO/water such that the final concentration c of test substance in the test batch was 50 μM. The DMSO concentration in the test batch was 5% (v/v). The reaction was started by addition of the sGC. The reaction mix was incubated at 37° C. for 15 to 20 minutes and then stopped by ice-cooling and addition of the stop reagent (50 mM EDTA, pH 8.0). An aliquot of 50 μl was taken and employed for the determination of the cGMP content using the acetylation protocol of the Amersham cGMP EIA kit. The absorption of the samples was measured at 450 nm (reference wavelength 620 nm) in a microtiter plate reading apparatus. The cGMP concentration was determined by means of a calibration curve, which was obtained under the same experimental conditions. The activation of the sGC by a test substance is indicated as n-fold stimulation of the basal enzyme activity which was found in the control experiments (with solvent instead of test substance), calculated according to the formula n-fold stimulation=$[cGMP]_{test\ substance}/[cGMP]_{control}$.

The following results were obtained:

| Compound of Example No. | n-fold stimulation at c = 50 μM |
|---|---|
| 15 | 7 |
| 16 | 34 |
| 25 | 6 |
| 26 | 5 |
| 30 | 6 |
| 32 | 15 |
| 33 | 5 |
| 34 | 35 |
| 35 | 7 |
| 40 | 8 |
| 41 | 9 |
| 42 | 10 |
| 43 | 23 |
| 44 | 7 |
| 45 | 7 |
| 48 | 9 |
| 49 | 5 |
| 50 | 8 |

What is claimed is:
1. A compound of formula I,

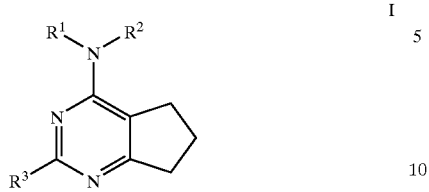

wherein $R^1$ and $R^2$, which are independent of one another and can be identical or different, are selected from the group consisting of hydrogen, $(C_1-C_8)$-alkyl, wherein the $(C_1-C_8)$-alkyl is unsubstituted or substituted by at least one identical or different substituents chosen from hydroxyl, $(C_1-C_4)$-alkoxy, $(C_1-C_4)$-alkyl-S(O)$_m$—, phenyl, naphthyl and pyridyl, $(C_3-C_9)$-cycloalkyl, wherein the $(C_3-C_9)$-cycloalkyl is unsubstituted or substituted by at least one identical or different substituents chosen from $(C_1-C_4)$-alkyl, hydroxyl, amino and benzyl, and a radical of a 5-membered to 7-membered saturated heterocyclic ring which contains one or two identical or different hetero ring members chosen from O, $NR^{10}$ and S(O)$_m$, wherein the 5-membered to 7-membered saturated heterocyclic ring is unsubstituted or substituted by at least one identical or different substituents chosen from $(C_1-C_4)$-alkyl, hydroxyl and aryl-$(C_1-C_4)$-alkyl, wherein the radicals phenyl, naphthyl, pyridyl and benzyl contained in the radicals $R^1$ or $R^2$ are unsubstituted or substituted in the aromatic ring by at least one identical or different substituents chosen from halogen, $(C_1-C_4)$-alkyl, phenyl, $CF_3$, $NO_2$, OH, —O—$(C_1-C_4)$-alkyl, —O—$(C_2-C_4)$-alkyl-O—$(C_1-C_4)$-alkyl, $(C_1-C_2)$-alkylenedioxy, $NH_2$, —NH—$(C_1-C_4)$-alkyl, —N($(C_1-C_4)$-alkyl)$_2$, —NH—CHO, —NH—CO—$(C_1-C_4)$-alkyl, —CN, —CO—$NH_2$, —CO—NH—$(C_1-C_4)$-alkyl, —CO—N($(C_1-C_4)$-alkyl)$_2$, —CO—OH, —CO—O—$(C_1-C_4)$-alkyl, —CHO and —CO—$(C_1-C_4)$-alkyl, but where $R^1$ and $R^2$ cannot both simultaneously be hydrogen; or the radical $R^1R^2N$ is a radical, bonded via a ring nitrogen atom, of a 5-membered to 7-membered saturated heterocyclic ring which, in addition to the nitrogen atom carrying the radicals $R^1$ and $R^2$, can contain at least one further hetero ring member chosen from O and S(O)$_m$ wherein the 5-membered to 7-membered saturated heterocyclic ring is unsubstituted or substituted by at least one identical or different substituents chosen from $(C_1-C_4)$-alkyl, hydroxyl, $(C_1-C_4)$-alkoxy and $R^{11}R^{12}N$;

$R^3$ is aryl but cannot be unsubstituted phenyl;

$R^{10}$ is hydrogen, $(C_1-C_4)$-alkyl, aryl-$(C_1-C_4)$-alkyl-, hydroxy-$(C_1-C_4)$-alkyl-, hydroxycarbonyl-$(C_1-C_4)$-alkyl-, (($(C_1-C_4)$-alkoxycarbonyl)-$(C_1-C_4)$-alkyl-, $R^{11}R^{12}N$—CO—$(C_1-C_4)$-alkyl-, $R^{13}$—$SO_2$— or aryl;

$R^{11}$ and $R^{12}$ are identical or different radicals selected from the group consisting of hydrogen and $(C_1-C_4)$-alkyl;

$R^{13}$ is $(C_1-C_4)$-alkyl, aryl or $R^{11}R^{12}N$;

wherein aryl is chosen from phenyl, naphthyl and heteroaryl, and wherein said phenyl, naphthyl, and heteroaryl is unsubstituted or substituted by at least one identical or different substituents chosen from halogen, $(C_1-C_4)$-alkyl, phenyl, $CF_3$, $NO_2$, OH, —O—$(C_1-C_4)$-alkyl, —O—$(C_2-C_4)$-alkyl-O—$(C_1-C_4)$-alkyl, $(C_1-C_2)$-alkylenedioxy, $NH_2$, —NH—$(C_1-C_4)$-alkyl, —N($(C_1-C_4)$-alkyl)$_2$, —NH—CHO, —NH—CO—$(C_1-C_4)$-alkyl, —CN, —CO—$NH_2$, —CO—NH—$(C_1-C_4)$-alkyl, —CO—N($(C_1-C_4)$-alkyl)$_2$, —CO—OH, —CO—O—$(C_1-C_4)$-alkyl, —CHO and —CO—$(C_1-C_4)$-alkyl;

wherein heteroaryl is chosen from a radical of a monocyclic 5-membered aromatic heterocycle, a radical of a monocyclic 6-membered aromatic heterocycle, a radical of a bicyclic 8-membered aromatic heterocycle, a radical of a bicyclic 9-membered aromatic heterocycle, and a radical of a bicyclic 10-membered aromatic heterocycle, each of which contain at least one identical or different ring heteroatoms chosen from N, O and S; and m is 0, 1 or 2;

or a salt thereof, in any stereoisomeric form, or a mixture of any such compounds in any ratio.

2. A compound as claimed in claim 1, wherein one of the radicals $R^1$ and $R^2$ is selected from the group consisting of $(C_1-C_8)$-alkyl which is unsubstituted or substituted by at least one identical or different substituents chosen from hydroxyl, $(C_1-C_4)$-alkoxy, $(C_1-C_4)$-alkyl-S(O)$_m$—, unsubstituted or substituted phenyl and unsubstituted or substituted naphthyl, and $(C_3-C_9)$-cycloalkyl which is unsubstituted or substituted by at least one identical or different substituents chosen from $(C_1-C_4)$-alkyl, hydroxyl, amino and unsubstituted or substituted benzyl;

and the other of the radicals $R^1$ and $R^2$ is selected from the group consisting of hydrogen, $(C_1-C_8)$-alkyl which is unsubstituted or substituted by at least one identical or different substituent chosen from hydroxyl, $(C_1-C_4)$-alkoxy, $(C_1-C_4)$-alkyl-S(O)$_m$—, unsubstituted or substituted phenyl and unsubstituted or substituted naphthyl, and $(C_3-C_9)$-cycloalkyl which is unsubstituted or substituted by at least one identical or different substituent chosen from $(C_1-C_4)$-alkyl, hydroxyl, amino and unsubstituted or substituted benzyl; or $R^1R^2N$ is a radical, bonded via a ring nitrogen atom, chosen from a 5-membered saturated heterocyclic ring, a 6-membered saturated heterocyclic ring and a 7-membered saturated heterocyclic ring, wherein said $R^1R^2N$ radical in addition to the nitrogen atom carrying the radicals $R^1$ and $R^2$, can additionally contain a further hetero ring member chosen from an oxygen atom and S(O)$_m$ and wherein said $R^1R^2N$ radical is unsubstituted or substituted by at least one identical or different substituents chosen from $(C_1-C_4)$-alkyl, hydroxyl, $(C_1-C_4)$-alkoxy and $R^{11}R^{12}N$;

or a salt thereof, in any stereoisomeric form, or a mixture of any such compounds in any ratio.

3. A compound as claimed in claim 1, wherein one of the radicals $R^1$ and $R^2$ is selected from the group consisting of $(C_1-C_4)$-alkyl which is unsubstituted or substituted by at least one identical or different substituents chosen from hydroxyl, $(C_1-C_4)$-alkoxy, $(C_1-C_4)$-alkyl-S(O)$_m$—, unsubstituted or substituted phenyl and unsubstituted or substituted naphthyl, and $(C_3-C_9)$-cycloalkyl which is unsubstituted or substituted by at least one identical or different substituents chosen from $(C_1-C_4)$-alkyl, hydroxyl, amino and unsubstituted or substituted benzyl;

and the other of the radicals $R^1$ and $R^2$ is hydrogen, or the radicals $R^1$ and $R^2$ are identical or different $(C_1-C_4)$-alkyl which is unsubstituted or substituted by at least one identical or different substituents chosen from hydroxyl, $(C_1-C_4)$-alkoxy, $(C_1-C_4)$-alkyl-S(O)$_m$—, unsubstituted or substituted phenyl and unsubstituted or substituted naphthyl;

or a salt thereof, in any stereoisomeric form, or a mixture of any such compounds in any ratio.

4. A compound as claimed in claim 1, in which one of the radicals $R^1$ and $R^2$ is $(C_3-C_9)$-cycloalkyl which is unsubstituted or substituted by at least one identical or different substituents chosen from $(C_1-C_4)$-alkyl, hydroxyl, amino and benzyl, and the other of the radicals $R^1$ and $R^2$ is hydrogen;

or a salt thereof, in any stereoisomeric form, or a mixture of any such compounds in any ratio.

5. A compound as claimed in claim 1, in which $R^1R^2N$ is a radical chosen from piperidino, morpholino and thiomorpholino (and its S-oxide and S,S-dioxide);

or a salt thereof, in any stereoisomeric form, or a mixture of any such compounds in any ratio.

6. A compound as claimed in claim 1, in which $R^3$ is substituted phenyl;

or a salt thereof, in any stereoisomeric form, or a mixture of any such compounds in any ratio.

7. A process for the preparation of compounds as claimed in claim 1, which comprises activating a 4-hydroxypyrimidine of the formula IV and then reacting it with an amine of the formula VI,

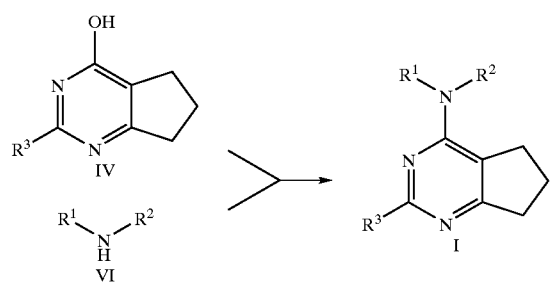

wherein $R^1$, $R^2$ and $R^3$ are defined as in claim 1.

8. A pharmaceutical composition comprising at least one of the compound chosen from the compounds as claimed in claim 1 and their physiologically tolerable salts, and a pharmaceutically tolerable carrier.

9. A method of activating soluble guanylate cyclase comprising addition of an effective amount of at least one compound chosen from the compounds as claimed in claim 1 and their physiologically tolerable salts.

10. A method of treating or preventing cardiovascular disorders, endothelial dysfunction, diastolic dysfunction, atherosclerosis, high blood pressure, angina pectoris, thromboses, restenoses, myocardial infarct, strokes, cardiac insufficiency, pulmonary hypertension, erectile dysfunction, bronchial asthma, chronic renal insufficiency, diabetes or liver cirrhosis or for improving restricted learning capacity or memory power, comprising administering to a patient in need thereof an effective amount of at least one compound chosen from the compounds as claimed in claim 1 and their physiologically tolerable salts.

11. A method of activating soluble guanylate cyclase comprising administering to a patient in need thereof an effective amount of at least one compound chosen from the compounds as claimed in claim 1 and their physiologically tolerable salts.

* * * * *

UNITED STATES PATENT AND TRADEMARK OFFICE
CERTIFICATE OF CORRECTION

PATENT NO. : 6,627,628 B1
DATED : September 30, 2003
INVENTOR(S) : Schindler et al.

It is certified that error appears in the above-identified patent and that said Letters Patent is hereby corrected as shown below:

<u>Title page,</u>
Item [75], Inventors, "Soden (DE)" should read -- Bad Soden (DE) --.

<u>Column 22,</u>
Line 23, after "A method of treating", delete "or preventing".

Signed and Sealed this

Twenty-third Day of March, 2004

JON W. DUDAS
*Acting Director of the United States Patent and Trademark Office*